(12) United States Patent
Thornton et al.

(10) Patent No.: US 9,208,429 B2
(45) Date of Patent: Dec. 8, 2015

(54) MULTIPLE DELIVERY DEVICE COUNTER AND COUNTING METHOD

(71) Applicant: Teleflex Medical Incorporated, Research Triangle Park, NC (US)

(72) Inventors: Curtis Thornton, Pittsboro, NC (US); Lynn J. Willett, Pittsboro, NC (US)

(73) Assignee: TELEFLEX MEDICAL INCORPORATED, Research Triangle Park, NC (US)

( * ) Notice: Subject to any disclaimer, the term of this patent is extended or adjusted under 35 U.S.C. 154(b) by 371 days.

(21) Appl. No.: 13/755,346

(22) Filed: Jan. 31, 2013

(65) Prior Publication Data

US 2014/0209670 A1   Jul. 31, 2014

(51) Int. Cl.
| | |
|---|---|
| G01P 3/10 | (2006.01) |
| G06M 1/00 | (2006.01) |
| G06M 1/36 | (2006.01) |
| G06M 1/08 | (2006.01) |
| A61B 17/128 | (2006.01) |
| A61B 19/00 | (2006.01) |

(52) U.S. Cl.
CPC ............ *G06M 1/083* (2013.01); *A61B 17/1285* (2013.01); *A61B 2019/4815* (2013.01)

(58) Field of Classification Search
CPC ....... G06M 1/062; G06M 1/083; G06M 1/02; G06M 1/22
USPC ...................... 235/103, 115, 118, 122, 144 D
See application file for complete search history.

(56) References Cited

U.S. PATENT DOCUMENTS

| | | | |
|---|---|---|---|
| 3,300,131 A | * | 1/1967 | Juhas ............................ 235/103 |
| 4,821,300 A | | 4/1989 | Pollmann |
| 5,312,023 A | | 5/1994 | Green et al. |
| 5,326,013 A | | 7/1994 | Green et al. |
| 5,364,001 A | | 11/1994 | Bryan |
| 5,397,046 A | | 3/1995 | Savage et al. |
| 5,431,322 A | | 7/1995 | Green et al. |
| 5,448,042 A | | 9/1995 | Robin et al. |
| 5,456,401 A | | 10/1995 | Green et al. |
| 5,462,558 A | | 10/1995 | Kolesa et al. |
| 5,472,132 A | | 12/1995 | Savage et al. |
| 5,478,003 A | | 12/1995 | Green et al. |
| 5,482,197 A | | 1/1996 | Green et al. |
| 5,487,499 A | | 1/1996 | Sorrentino et al. |
| 5,519,197 A | | 5/1996 | Robin et al. |
| 5,584,425 A | | 12/1996 | Savage et al. |
| 5,636,780 A | | 6/1997 | Green et al. |
| 5,645,209 A | | 7/1997 | Green et al. |
| 5,645,553 A | | 7/1997 | Kolesa et al. |
| 5,647,526 A | | 7/1997 | Green et al. |
| 5,709,334 A | | 1/1998 | Sorrentino et al. |
| 5,711,472 A | | 1/1998 | Bryan |
| 5,772,673 A | | 6/1998 | Cuny et al. |
| 5,918,791 A | | 7/1999 | Sorrentino et al. |

(Continued)

*Primary Examiner* — Laura Gudorf
(74) *Attorney, Agent, or Firm* — Baker & Hostetler LLP

(57) ABSTRACT

A counter mechanism includes: a counter housing including a shaft and a hole; a first set of cam teeth located in the hole; a striker located in the hole and configured to move axially with respect to the hole having a second set of cam teeth; a counter wheel hub having a third set of cam teeth configured to communicate with both the first and second set of cam teeth, the counter wheel hub also having an actuator; and a counter wheel having an actuation feature configured to communicate with the actuator to cause the counter wheel to rotate when the counter wheel hub rotates. A method for counting dispensed items may also be described.

19 Claims, 2 Drawing Sheets

(56) References Cited

U.S. PATENT DOCUMENTS

| | | |
|---|---|---|
| 5,969,315 A | 10/1999 | Schulze |
| 6,082,358 A | 7/2000 | Scarrott et al. |
| D439,534 S | 3/2001 | Scarrott et al. |
| 6,250,532 B1 | 6/2001 | Green et al. |
| D447,432 S | 9/2001 | Scarrott et al. |
| 6,328,037 B1 | 12/2001 | Scarrott et al. |
| 6,336,453 B1 | 1/2002 | Scarrott et al. |
| D456,292 S | 4/2002 | Scarrott et al. |
| 6,619,529 B2 | 9/2003 | Green et al. |
| 6,644,532 B2 | 11/2003 | Green et al. |
| 6,729,330 B2 | 5/2004 | Scarrott et al. |
| 6,761,161 B2 | 7/2004 | Scarrott et al. |
| 6,779,715 B2 | 8/2004 | Williams |
| 6,877,647 B2 | 4/2005 | Green et al. |
| 6,926,002 B2 | 8/2005 | Scarrott et al. |
| 6,953,039 B2 | 10/2005 | Scarrott et al. |
| 7,296,724 B2 | 11/2007 | Green et al. |
| 7,341,057 B2 | 3/2008 | Scarrott et al. |
| 7,350,693 B2 | 4/2008 | Roper |
| 7,464,848 B2 | 12/2008 | Green et al. |
| 7,516,738 B2 | 4/2009 | Scarrott et al. |
| 7,543,731 B2 | 6/2009 | Green et al. |
| 7,568,481 B2 | 8/2009 | Scarrott et al. |
| 7,637,917 B2 | 12/2009 | Whitfield et al. |
| 7,644,848 B2 | 1/2010 | Swayze et al. |
| 7,650,883 B2 | 1/2010 | Scarrott et al. |
| 7,717,926 B2 | 5/2010 | Whitfield et al. |
| 7,757,688 B2 | 7/2010 | Scarrott et al. |
| 7,819,886 B2 | 10/2010 | Whitfield et al. |
| 7,861,907 B2 | 1/2011 | Green et al. |
| 7,891,533 B2 | 2/2011 | Green et al. |
| 7,905,380 B2 | 3/2011 | Shelton et al. |
| 7,905,890 B2 | 3/2011 | Whitfield et al. |
| 8,056,565 B2 | 11/2011 | Zergiebel |
| 8,074,643 B2 | 12/2011 | Scarrott et al. |
| 8,082,873 B2 | 12/2011 | Nuttall |
| 8,196,796 B2 | 6/2012 | Shelton et al. |
| 8,267,946 B2 | 9/2012 | Whitfield et al. |
| 8,282,655 B2 | 10/2012 | Whitfield et al. |
| 8,336,556 B2 | 12/2012 | Zergiebel |
| 8,357,171 B2 | 1/2013 | Whitfield et al. |
| 8,382,773 B2 | 2/2013 | Whitfield et al. |
| 2004/0167545 A1 | 8/2004 | Sadler et al. |
| 2009/0228024 A1 | 9/2009 | Whitfield et al. |
| 2010/0057106 A1 | 3/2010 | Sorrentino et al. |
| 2010/0222790 A1 | 9/2010 | Whitfield et al. |
| 2011/0034910 A1 | 2/2011 | Ross et al. |
| 2011/0082474 A1 | 4/2011 | Bindra et al. |
| 2011/0137323 A1 | 6/2011 | Malkowski et al. |
| 2011/1155786 | 6/2011 | Shelton, IV |
| 2011/0290854 A1 | 12/2011 | Timm et al. |
| 2012/0116420 A1 | 5/2012 | Sorrentino et al. |
| 2012/0132450 A1 | 5/2012 | Timm et al. |
| 2012/0222672 A1 | 9/2012 | Scarrott et al. |

\* cited by examiner

MULTIPLE DELIVERY DEVICE COUNTER AND COUNTING METHOD

FIELD OF THE INVENTION

The present invention relates generally to a counting device. More particularly, the present invention relates to a device and method for counting how many objects have been delivered by an applier.

BACKGROUND OF THE INVENTION

More and more surgery is conducted with the aid of surgical devices. For example, laparoscopic surgery may include the use of an automatic ligation device. The automatic ligation device, when actuated by a surgeon, may deploy a clip to close off a blood vessel. In some instances each time a trigger or other lever is actuated by the surgeon, the ligation device may deploy a clip. Clips may be stored in a magazine within the applier. Once the clip has been deployed it is no longer connected to or otherwise controlled by the applier. It may be desirable for the surgeon to know how many clips have been deployed.

Accordingly, it may be desirable to provide a device that counts how many clips have been deployed by an applier.

SUMMARY OF THE INVENTION

The foregoing needs are met, to a great extent, by the present invention, wherein in one aspect an apparatus is provided that in some embodiments keeps track of how many times an applier has been actuated or how many objects have been deployed from the applier.

In accordance with one embodiment of the present invention, a counter mechanism may be provided. The counter mechanism may include: a counter housing including a shaft and a hole; a first set of cam teeth located in the hole; a striker located in the hole and configured to move axially with respect to the hole having a second set of cam teeth; a counter wheel hub having a third set of cam teeth configured to communicate with both the first and second set of cam teeth, the counter wheel hub also having an actuator; and a counter wheel having an actuation feature configured to communicate with the actuator to cause the counter wheel to rotate when the counter wheel hub rotates.

In accordance with another embodiment of the present invention, a method for counting dispensed items may be provided. The method may include: engaging a first set of cam teeth and a second set of cam teeth with a third set of cam teeth; moving a striker axially through a hole in the counter housing to disengage the third set of cam teeth from the first set of cam teeth; rotating a wheel hub until the third set of cam teeth come to rest in a notch in the second set of cam teeth; and rotating a counter wheel when the counter wheel hub rotates.

In accordance with yet another embodiment of the present invention, a counter mechanism may be provided. The counter mechanism may include: a counter housing including a shaft and a hole; a first means for engaging located in the hole; a striker located in the hole and configured to move axially with respect to the hole having a second means for engaging; and a counter wheel hub having a third means for engaging configured to communicate with both the first and second means for engaging.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
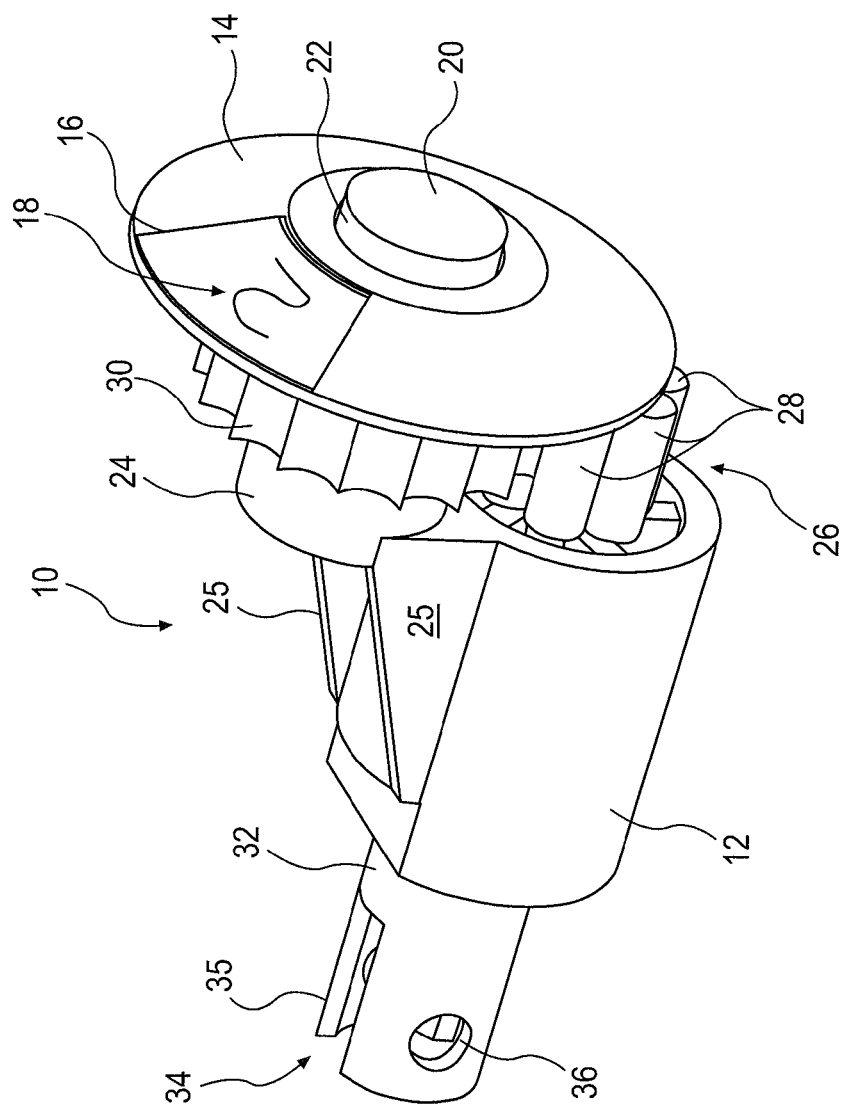
FIG. 1 is an isometric view illustrating a multi-delivery device counter in accordance with an embodiment of the invention.

The invention will now be described with reference to the drawing figures, in which like reference numerals refer to like parts throughout. An embodiment in accordance with the present invention provides a device for counting objects that may be delivered by a multi-delivery device. For example, and automatic clip applier such as the one shown and described in U.S. patent application Ser. No. 13/618,215 filed Sep. 14, 2012, Titled "Automatic Surgical Ligation Clip Applier" incorporated herein by reference in its entirety may deliver a ligation clip upon actuation of the trigger device such as the one shown and described herein may be attached to the automatic clip applier and keep track of how many clips have been applied.

An embodiment of the present inventive apparatus is illustrated in FIG. 1. FIG. 1 illustrates a counter 10. The counter 10 includes a counter housing 12. A counter wheel 14 is mounted onto the counter housing 12. The counter wheel 14 includes a counter wheel window 16. The counter wheel 16 may rotate and display indicia 18 that is located on a fixed disk 17. When the counter wheel 14 rotates, the counter wheel window 16 will also rotate thereby selectively covering and uncovering indicia 18 located on the fixed disk 17.

The counter wheel 14 and the fixed disk 17 both are supported on the wheel shaft 20. While the fixed disk 17 does not rotate about the wheel shaft 20, in some embodiments the counter wheel 14 does rotate. In other embodiments it may be the disk 17 that rotates and the counter wheel 14 that remains fixed.

The counter wheel 14 attaches to the counter housing 12 by the wheel shaft 20 extending through the hole 22 in the counter wheel 14. The wheel shaft 20 attaches to the counter housing 12 of the of the shaft mounting 24 the shaft mounting 24 may be connected to reinforcing fins 25 which are also attached to the counter housing 12.

The counter wheel 14 may be rotated by operation of the actuator wheel 26 teeth 28 interacting with the counter wheel actuation structure 30. As the actuator wheel 26 rotates, it causes the teeth 28 on the actuator wheel 26 to rotate and mesh with the counter wheel actuation structure 30 causing the wheel actuation structure 30 and counter wheel 14 to rotate. More discussion of the rotation the counter wheel 26 will be made in the description with respect to FIG. 2.

At the other end of the counter housing 12, the counter striker 32 is illustrated. The counter striker 32 is what the attaching structure 34 is connected to. The attaching structure 34 is used for attaching the counter 10 onto an instrument such as, for example, an automatic applier for counting items dispensed by the applier. The attaching mechanism 34 includes holes 36 and the slot 35.

Figure 2:
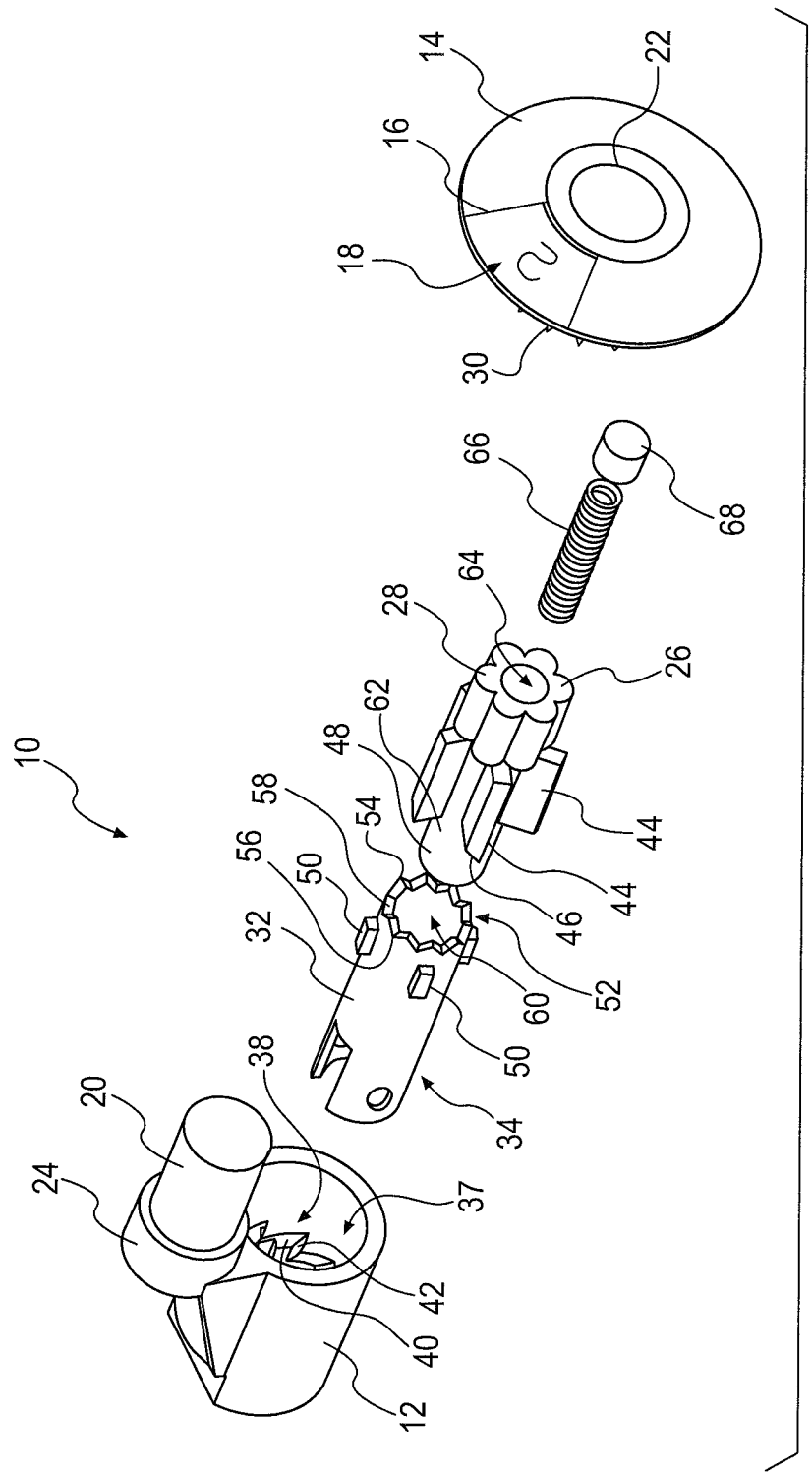
FIG. 2 is an exploded, isometric view of the multi-delivery device counter shown in FIG. 1.

Turning now to FIG. 2, an exploded view of the counter 10 is shown. The housing 12 includes the shaft mounting 24 to which the shaft 20 is mounted. The housing 12 defines a hole 37. Within the hole 37, cam teeth 38 are located. The cam teeth 38 include a sloped portion 40 and a vertical portion 42. The counter striker 32 is shown outside of the hole 37, but normally resides in the hole 37.

The cam teeth 38 are configured to interact with the cam teeth 44. The cam teeth 44 include a slanted edge 46. The cam teeth 44 located on the counter wheel hub 48. Normally, both the counter striker 32 and the counter wheel hub 48 are located in the hole 37 in the counter housing 12. The counter striker 32 includes stopping structure 50 which fit into slots in the hole 37 (not shown) to limit the rotation of the striker 32 in the housing 12 and to prevent the counter striker 32 from moving all the way through the hole 37 in the counter housing 12. The counter striker 32 also has a set of cam teeth 52. The cam teeth 52 and have high points 54 and low points 56 as well as a sloped area 58 located between the high points 54 and the low points 56. The cam teeth 52 are generally V-shaped. The cam teeth 52 on the striker 32 are located at a lower diameter that the teeth 38 in the housing 12.

The counter wheel hub 48 has the actuator wheel 26 attached. The actuator wheel 26 includes actuator teeth 28 which are configured to interact with the counter wheel actuation structure 30 located on the counter wheel 14. The counter wheel hub 48 and actuator wheel 26 include holes 60, 64. The spring 66 extends through the hole 64 in the counter wheel hub 48. While the shaft portion 62 of the wheel hub 48 extends into the hole 60 in the counter striker 32.

The spring 66 is capped with a spring cap 68 that when the counter 10 is assembled, urges against the counter wheel 14. As shown in FIGS. 1 and 2, the counter wheel 14 includes a window 16 to uncover indicia 18. The counter wheel 14 also includes a hole 22 to allow the counter wheel 14 to be mounted onto the wheel shaft 20. The counter wheel actuation structure 30 can barely be seen in FIG. 2 and is better shown in FIG. 1. One of ordinary skill in the art will appreciate that additional counter wheel actuation structure 30 is present on the back of the counter wheel 14 than what can be seen in the FIGURES.

The hole 64 in the wheel hub 48 is not a through hole. Thus, when assembled, the spring 66 is compressed between a floor in the hole 64 and the spring cap 68. As a result, the wheel hub 48 is biased axially toward the cam teeth 38. The spring cap 68 provides a smooth surface against the counter wheel 14 to limit friction force from the spring 66 which could otherwise impede the rotation of the counter wheel 14.

The cam teeth 52 on the striker 32 are located at a lower diameter that the teeth 38 in the housing 12. The cam teeth 52 on the striker 32 are offset from the cam teeth 38 in the housing 12. When assembled, the wheel hub 32 is centered in the housing 12 by cam teeth 44. The cam teeth 44 communicate with cam teeth 38 of the housing 12 and the cam teeth 52 of the striker 32.

The counter 10 is actuated by the axial movement of the striker 32 against the wheel hub 48. This axial movement of the striker 32 is the input into the counter 10 from an external device such as an automatic clip applier. Actuation of the clip applier results in the axial movement of the striker 32 against the wheel hub 48.

When the wheel hub 48 moves axially toward the counter wheel 14, the cam teeth 44 on the wheel hub 48 disengage from the cam teeth 38 in the housing 12. Due to the urging of the spring 66 against the wheel hub 48, the slanted edge 46 of the cam teeth slide along the sloped area 58 of the cam teeth 52 until the cam teeth 44 come to a stop in the low point 56 of the cam teeth 52. This cases partial rotation of the wheel hub 48.

When input to the counter 10 subsides, the spring 66 causes the striker 32 to return axially into the housing 12. The cam teeth 44 reengage the cam teeth 32. However, now the cam teeth 38 and 44 are misaligned. The force of the spring 66 will cause the slanted edge 46 of the cam teeth 44 to slide along the sloped portion 40 of the cam teeth 38 until the cam teeth 44 encounter and are stopped by the vertical portion 42 of the cam teeth 38. This sliding action causes the wheel hub 48 to rotate.

Due to the interaction between actuator wheel teeth 28 and the counter wheel actuation structure 30, when the wheel hub 48 rotates, the counter wheel 14 will also rotate.

As described above, the counter wheel 14 will rotate as a result of axial movement of the striker 32 in both the axial directions (toward and away from the housing 12). In some embodiments, when the striker 32 moves axially way from the housing 12, the counter wheel 14 will move half way to indicate a count and when the striker 32 returns toward the housing 12, the counter wheel 14 will move the rest of the way to indicate a count.

After reading this disclosure, one of ordinary skill in the art will understand how to select the pitch, dimensions for the teeth 28, 38, 44, and 52, the slanted edge 46, the sloped portions 40 and 58, and teeth (or gear) ratios to achieve a desired amount of rotation of the wheel hub 48.

The total number of objects that can be counted is related to the size and number of gear mesh and cam meshes. As mentioned above, these can be varied to allow for different counter configurations. The counter mechanism can be varied and customized to allow for different counts. The indicia 18 on the counter wheel 14 may also be varied or customized. For example, the indicia 18 may include, colors, symbols, characters such as numbers, letters, roman numerals, or any other desired indicia.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A counter mechanism comprising:
   a counter housing including a shaft and a hole;
   a first set of cam teeth located in the hole;
   a striker located in the hole and configured to move axially with respect to the hole having a second set of cam teeth;

a counter wheel hub having a third set of cam teeth configured to communicate with both the first and second set of cam teeth, the counter wheel hub also having an actuator; and a counter wheel having an actuation feature configured to communicate with the actuator to cause the counter wheel to rotate when the counter wheel hub rotates.

2. The counter mechanism of claim 1, further comprising a spring biasing the third set of cam teeth against the first set of cam teeth when the third set and first set of cam teeth are engaged with each other.

3. The counter mechanism of claim 2, further comprising a spring guide tapping one end of the spring.

4. The counter mechanism of claim 3, wherein the spring guide urges against the counter wheel.

5. The counter mechanism of claim 1, further comprising axial stops located on the striker and configured to limit axial movement of the striker within the hole in at least one axial direction.

6. The counter mechanism of claim 5, wherein the axial stops are configured to stop against the first set of cam teeth.

7. The counter mechanism of claim 1, wherein the first set of cam teeth include sloped portions and vertical portions.

8. The counter mechanism of claim 1, wherein the second set of cam teeth are V-shaped.

9. The counter mechanism of claim 1, wherein the third set of cam teeth include a slanted edge.

10. The counter mechanism of claim 1, wherein the counter wheel includes a window for displaying indicia associated with how many times the counter has been actuated.

11. The counter mechanism of claim 10, wherein the window rotates along with the counter wheel.

12. The counter mechanism of claim 1, wherein the counter wheel rotates on the shaft.

13. The counter mechanism of claim 1, wherein the actuator includes actuating teeth.

14. The counter mechanism of claim 1, wherein the striker is configured to move the counter wheel hub away from the first set of cam teeth thereby disengaging the third set of cam teeth from the first set of cam teeth when an item is being dispensed.

15. A method for counting dispensed items comprising:
engaging a first set of cam teeth and a second set of cam teeth with a third set of cam teeth;
moving a striker axially through a hole in a counter housing to disengage the third set of cam teeth from the first set of cam teeth;
rotating a wheel hub until the third set of cam teeth come to rest in a notch in the second set of cam teeth; and
rotating a counter wheel when the wheel hub rotates.

16. The method of claim 15 further including displaying indicia related to an amount of items dispensed in a window associated with the counter wheel.

17. The method of claim 15, further including moving the striker and wheel hub in an opposite axial direction to reengage the first set of cam teeth with the second set of cam teeth.

18. The method of claim 17, further including sliding the third set of cam teeth along a sloped portion of the first set of cam teeth until the second set of cam teeth butt against a vertical portion of the first set of cam teeth.

19. The method of claim 15 further including biasing the wheel hub to rotate.

* * * * *